Figure 16:
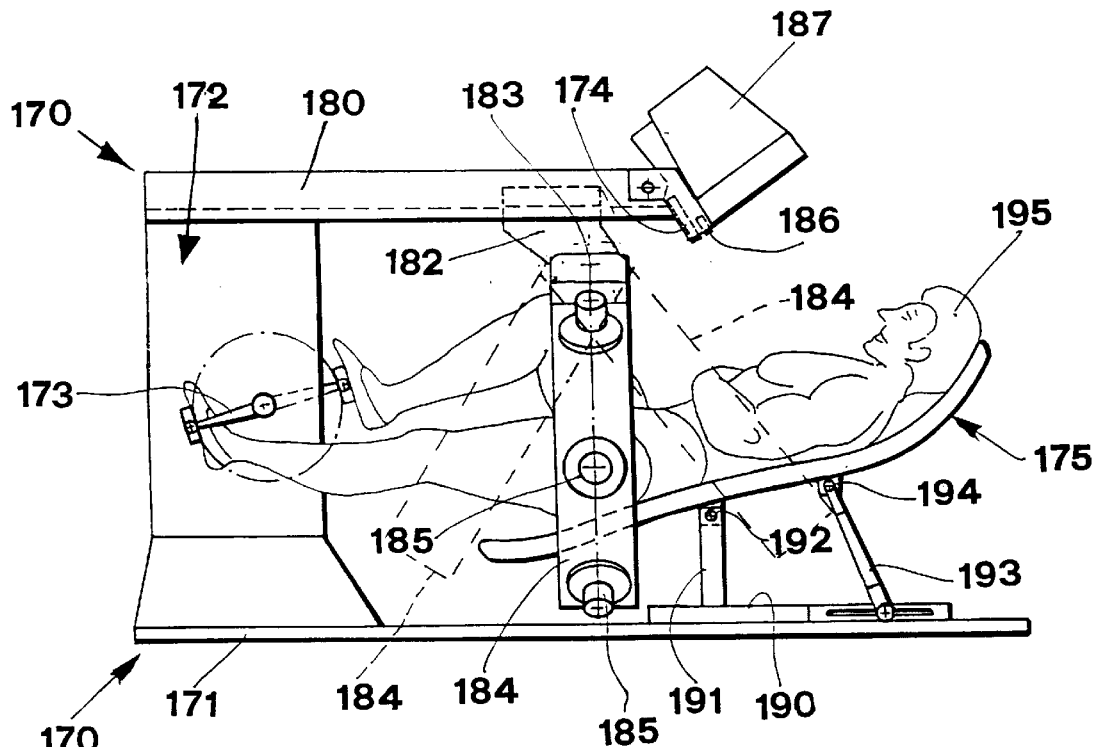

United States Patent

Marchesi

[11] Patent Number: 6,024,760
[45] Date of Patent: Feb. 15, 2000

[54] PROCESS AND EQUIPMENT FOR REDUCING ADIPOSE TISSUE IN SPECIFIC AREAS OF THE BODY BY COMBINED ACTION OF HEAT AND MUSCULAR ACTIVITY

[76] Inventor: Fabio Marchesi, Via Tavani 18, 24030 Mozzo, Italy

[21] Appl. No.: 08/732,264

[22] PCT Filed: Jun. 27, 1994

[86] PCT No.: PCT/IT94/00098

§ 371 Date: Oct. 16, 1996

§ 102(e) Date: Oct. 16, 1996

[87] PCT Pub. No.: WO95/30451

PCT Pub. Date: Nov. 16, 1995

[30] Foreign Application Priority Data

May 4, 1994 [IT] Italy ................................ MI94A0864

[51] Int. Cl.$^7$ ................................................. A61F 7/00
[52] U.S. Cl. .............................. 607/96; 607/88; 607/90; 607/100
[58] Field of Search ................... 607/88–90, 96, 607/99; 606/2–3, 9, 13

[56] References Cited

U.S. PATENT DOCUMENTS

| 4,742,235 | 5/1988 | Koji ........................................... 607/90 |
| 4,966,450 | 10/1990 | Mori ...................................... 607/88 X |
| 5,018,521 | 5/1991 | Campbell ................................. 607/98 |
| 5,616,140 | 4/1997 | Prescott ................................ 607/91 X |

*Primary Examiner*—Jeffrey R. Jastrzab
*Assistant Examiner*—Ryan Carter
*Attorney, Agent, or Firm*—Michael J. Striker

[57] ABSTRACT

Process and apparatus (170) for reducing adipose tissue in the human body (195), in certain areas by stimulating lipolysis through the presence of heat, provided by generators (185) of infrared rays (196) associated to muscular activity of an aerobic type, the generators (185) being fixed to specially made supports or mounted on gymnastic apparatus (170) and equipped so as to be directed onto the required areas of the body of the user (195) carrying out gymnastic exercises or muscular activity generally, either freely or with the aid of gymnastic apparatuses (170).

12 Claims, 7 Drawing Sheets

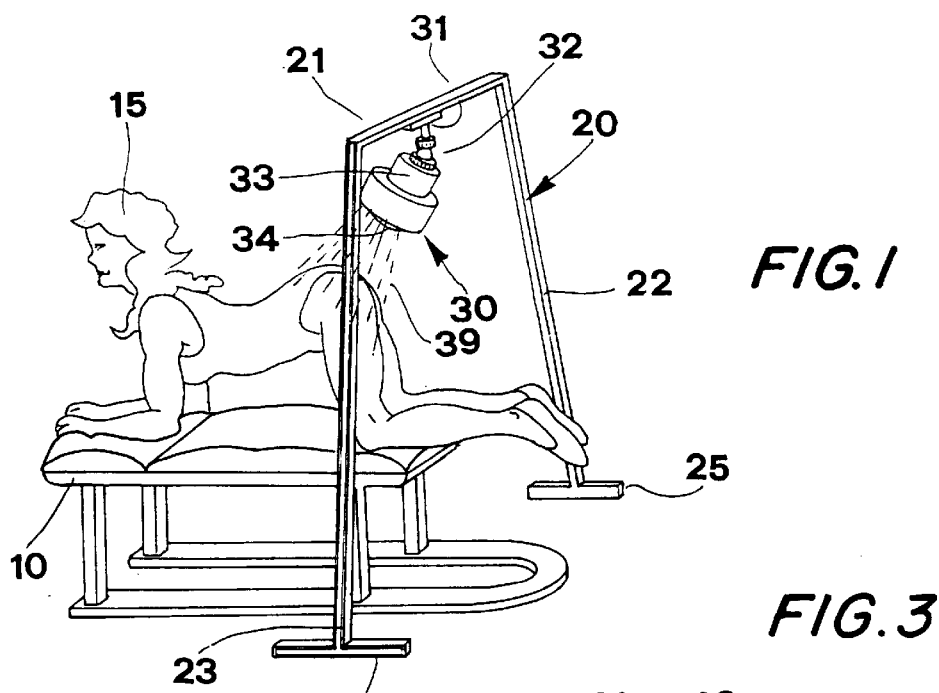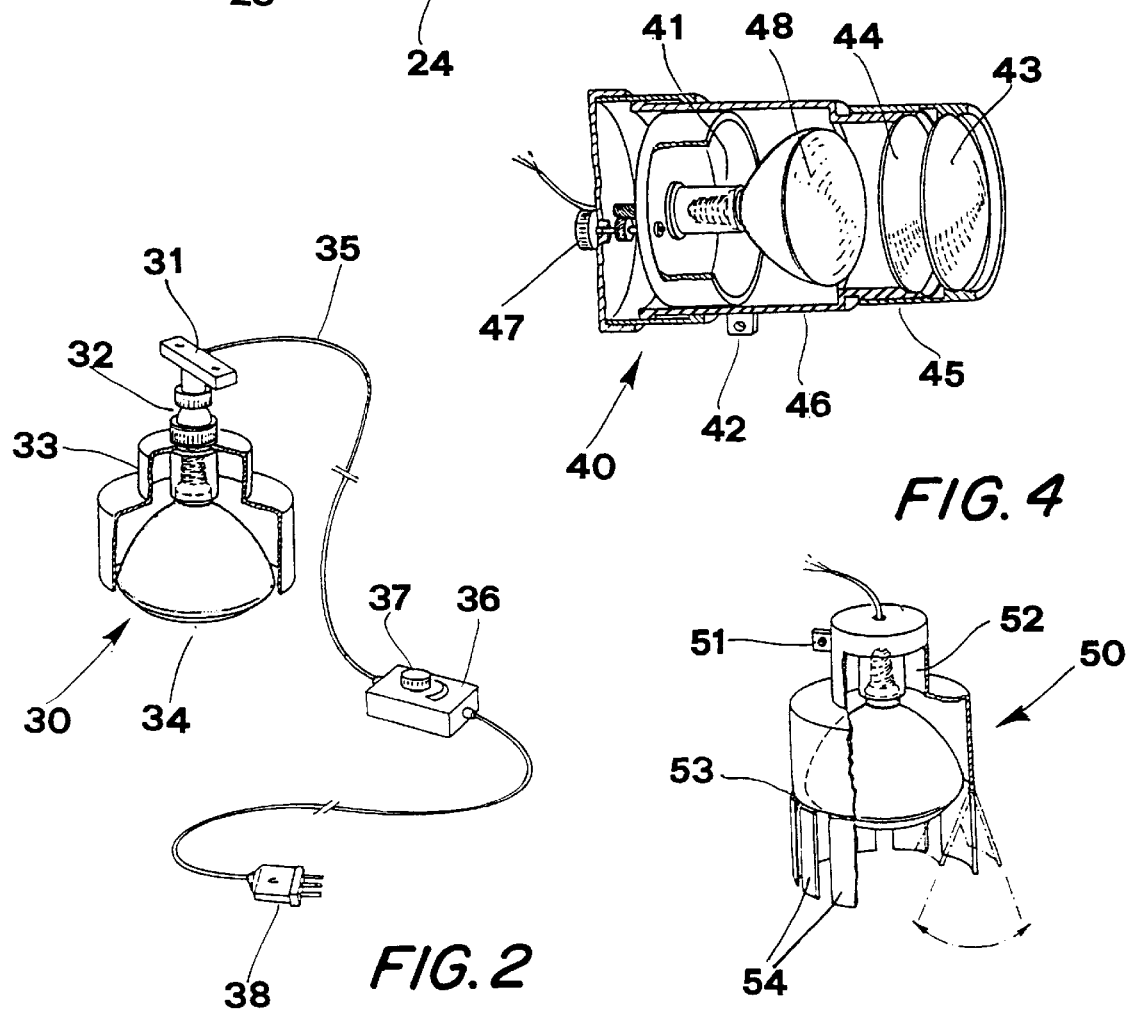

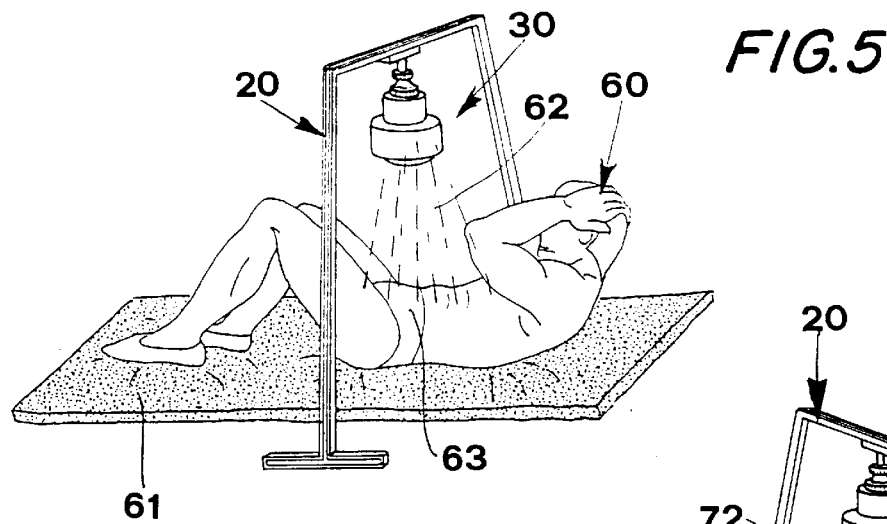
FIG. 5
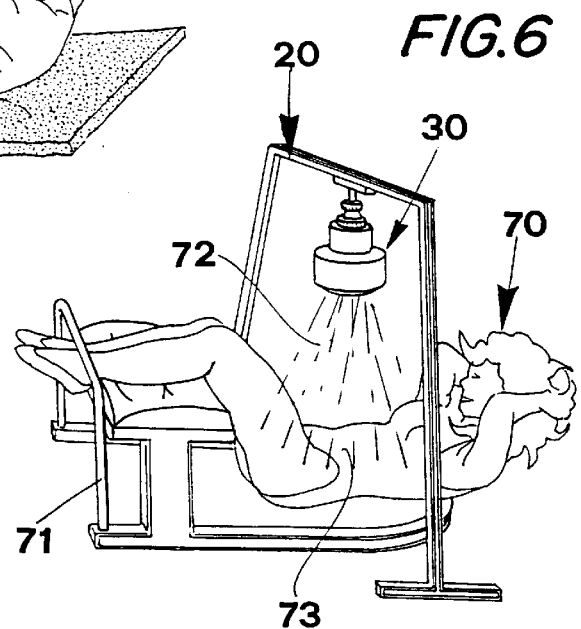
FIG. 6
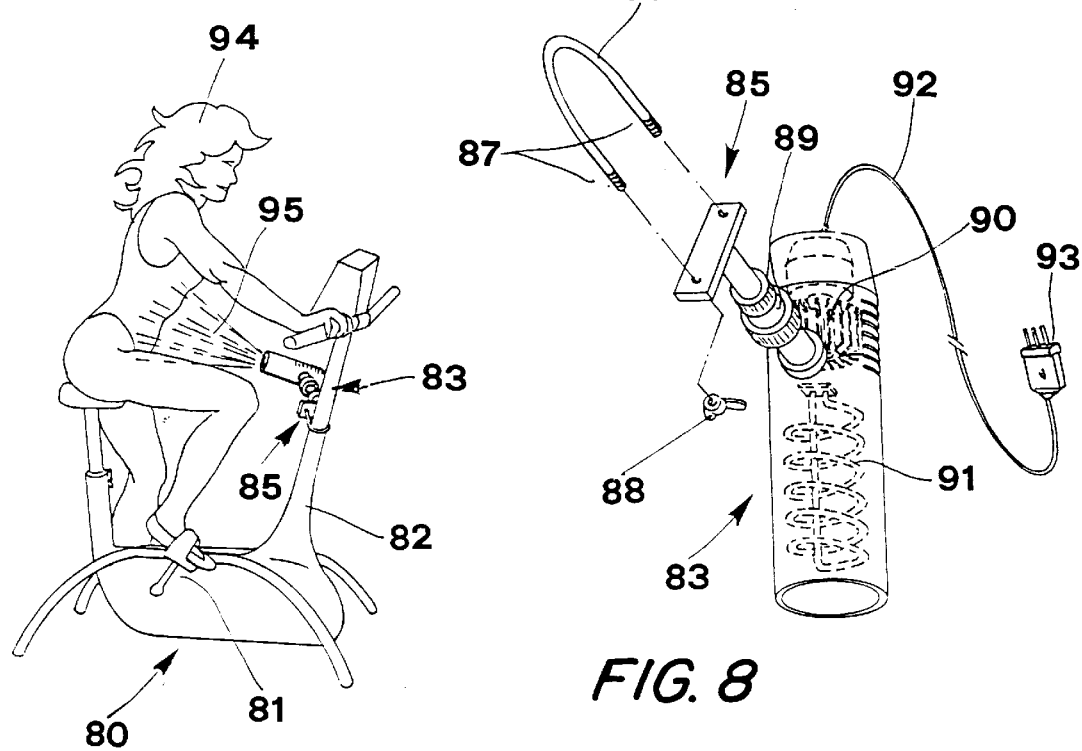
FIG. 7
FIG. 8

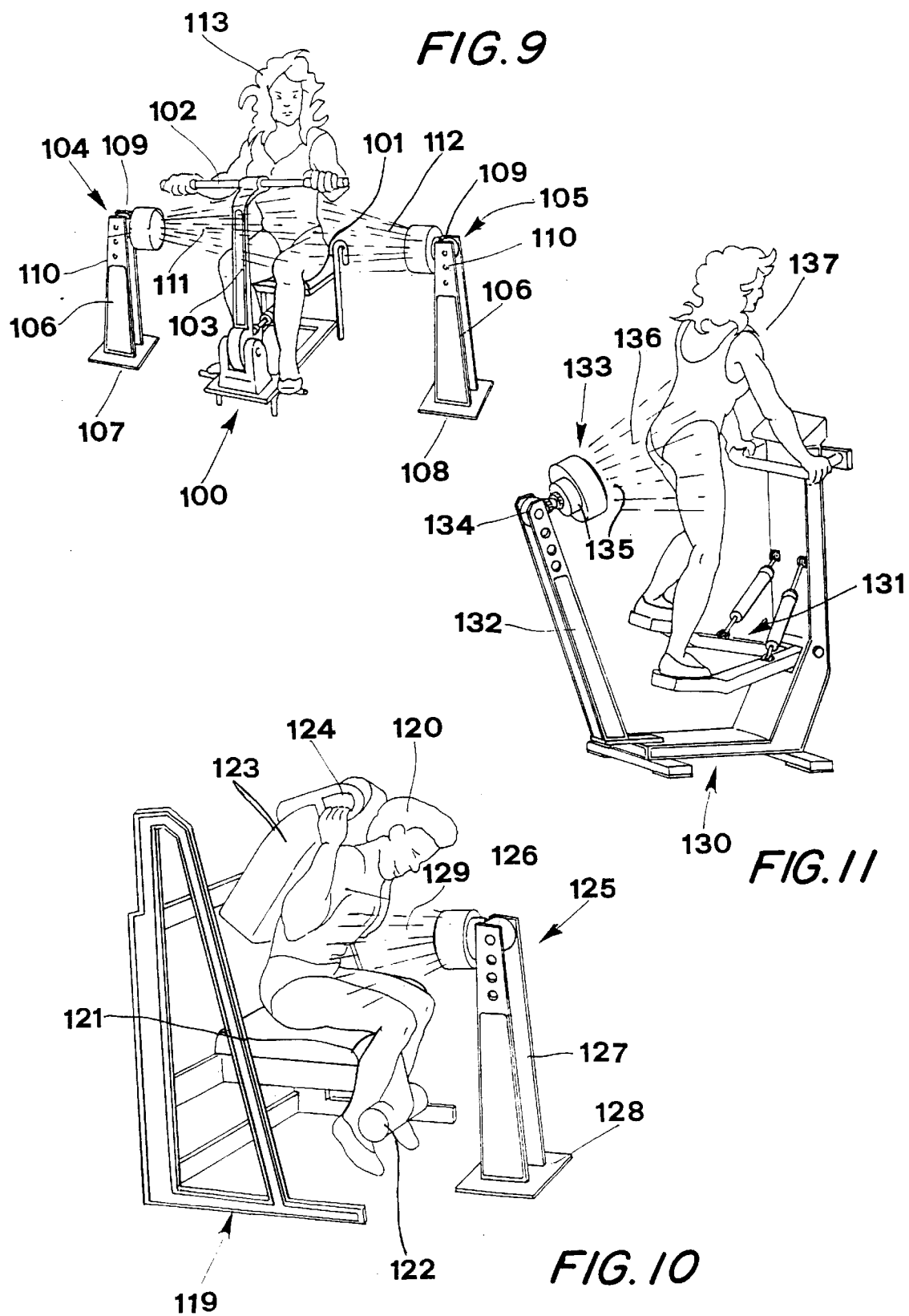

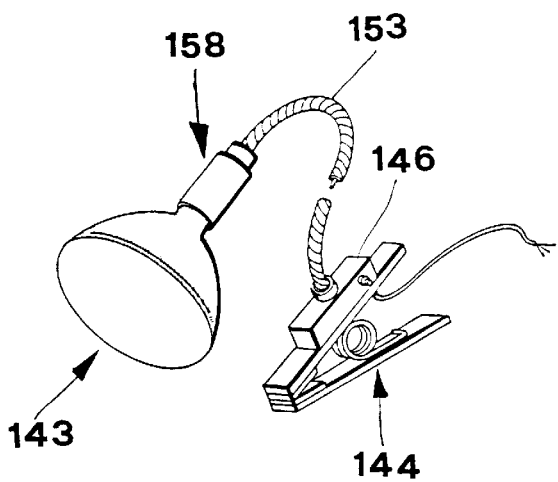
FIG. 14
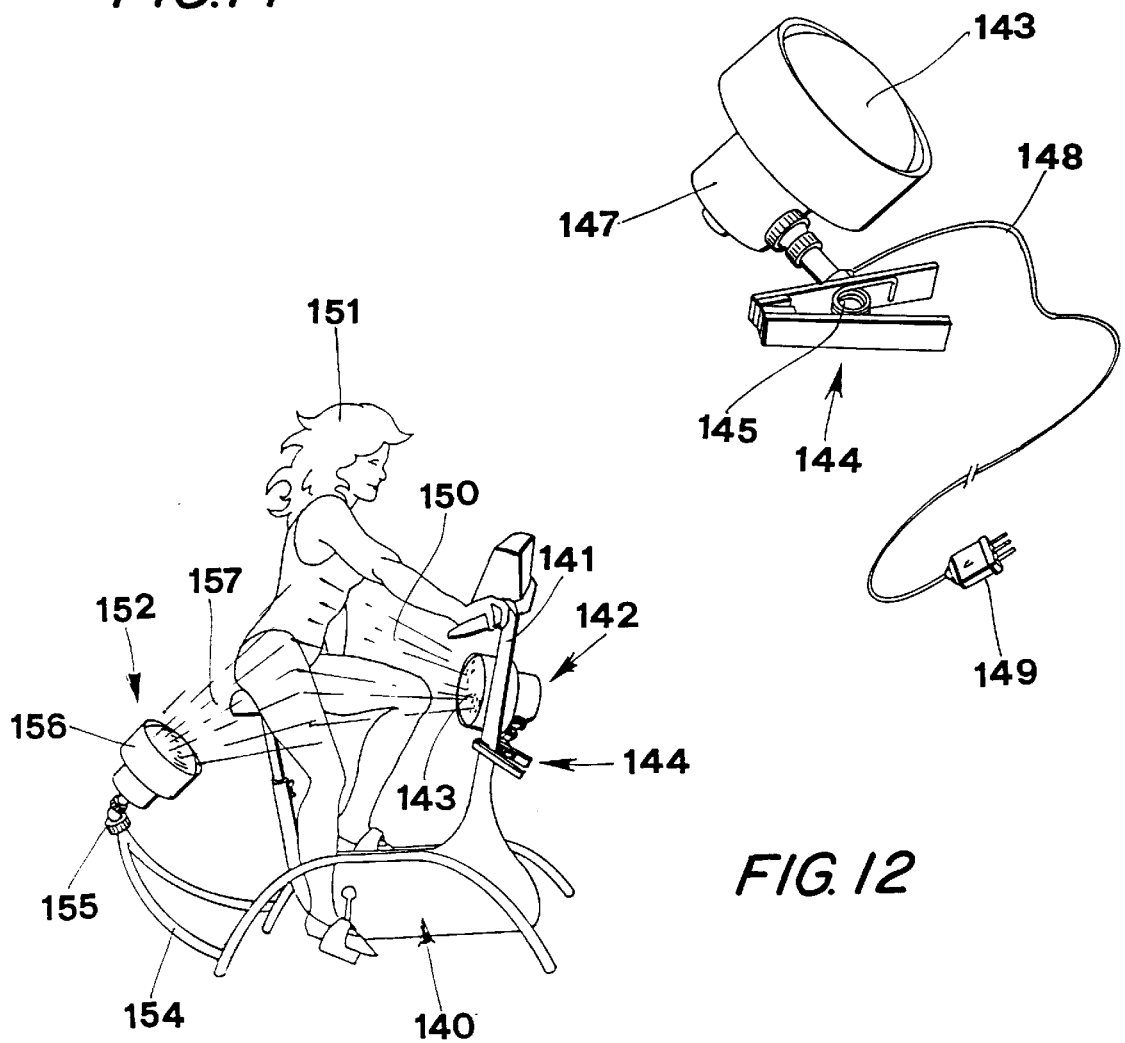
FIG. 13
FIG. 12

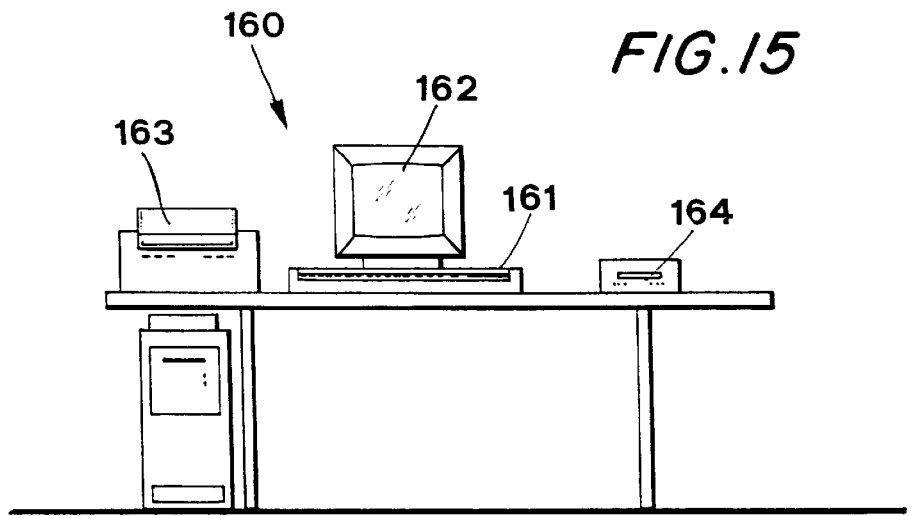
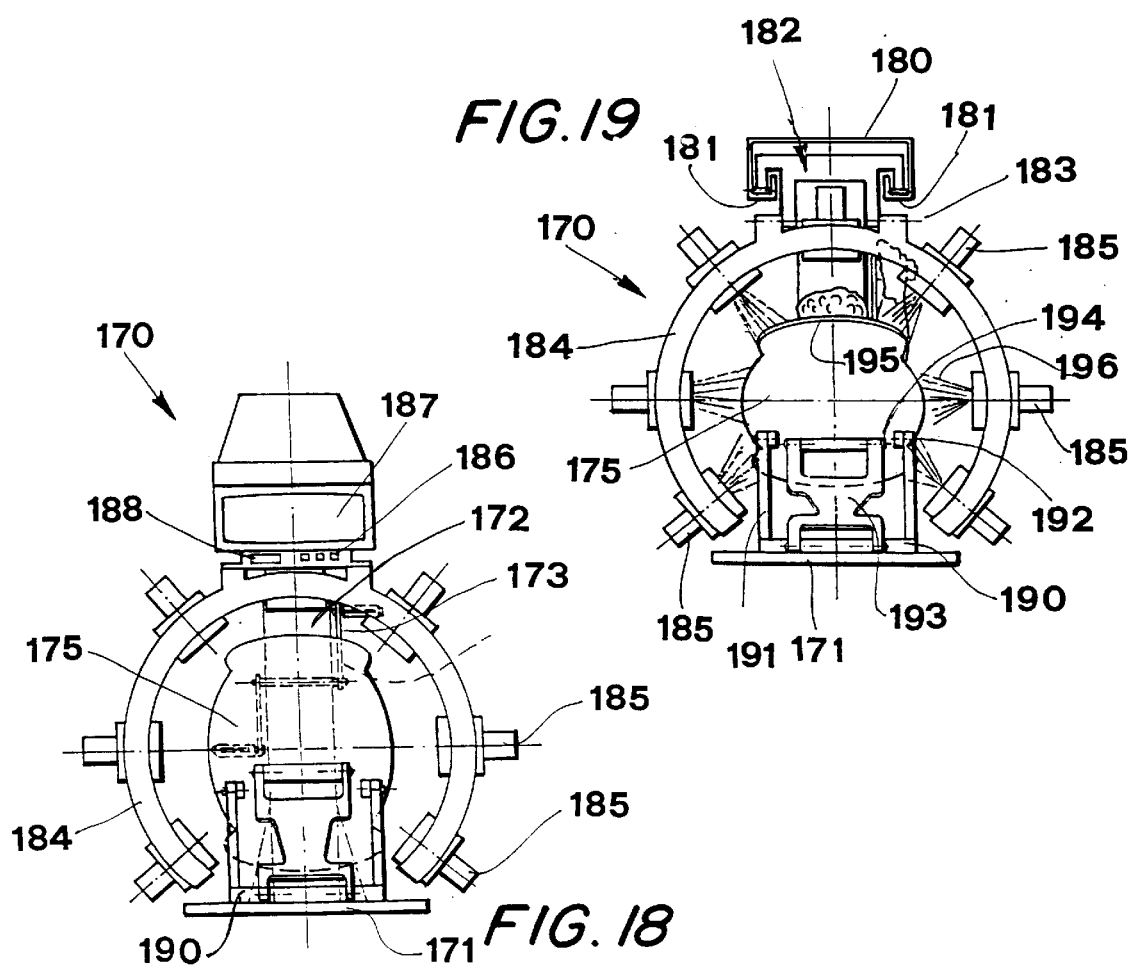

PROCESS AND EQUIPMENT FOR REDUCING ADIPOSE TISSUE IN SPECIFIC AREAS OF THE BODY BY COMBINED ACTION OF HEAT AND MUSCULAR ACTIVITY

The invention concerns methods and equipment for reducing adipose tissue.

It is known that fat contained in the body cells of animals fulfils two main functions: provision of energy and insulation of heat; about half of this fat is subcutaneous. Substantially 4% of total body fat is used to surround the heart,liver, brain, spleen and spinal column; there its function is protective and it should not be interfered with. Excess fat can however constitute a considerable risk to health, especially fat which accumulates on the abdomen (android obesity), and can lead to diabetes, vascular and other diseases; it is also anti-aesthetic and can even be the cause of social problems.

Fat can supply 80–90% of bodily energy since each gram of fat, containing about 20% of water, provides roughly 7 calories that can be transformed into the energy needed for various functions including muscular activity. Transformation of fat into energy implies oxidation of the atoms of hydrogen present in the fat molecules and it is therefore clear that, to remove excess fat, muscular activity may be resorted to.

The intensity of this activity is proportional to the rate of heart beat.

For example, if muscular activity produces a heart rate of 140 beats per minute, the body of a medium-sized person will burn about 12 calories per minute which means about 1.6 grams of fat per minute. Clearly there are limits to this method of eliminating fat as, in some people, a certain heart rate must not be exceeded. As already mentioned, subcutaneous fat also acts as a heat insulator. As the most important vital function is to keep body temperature at about 37° C., obviously the more heat a body receives and the more muscular activity it carries out, the less subcutaneous fat will it produce or retain.

As temperature rises the function of heat insulation will be less necessary and may even be negative, so that the body eliminates heat by perspiration and by using accumulated fat for energy. With this premise it is evident that adipose tissue can be reduced by lipolysis, burning calories and therefore fat cells. By carrying out muscular activity, lipolysis can be stimulated locally and direct heat applied to the fat.

But it is just the insulating characteristics of fat that make exothermal heating difficult whether by contact or by convection as, for example, by warm air being directed by a generator onto adipose tissue.

Similarly, by warming an actively working muscle by conduction, the effect on the fat is minimal and the heat so applied does not penetrate.

It is also known that a characteristic of infrared rays with short waves of a length greater than 0.8 microns, is that of heating body tissues and also penetrating them in depth.

Subject of the invention is a process based on the association of muscular activity, both free and using gymnastic equipment, with heat which is directed especially inside the adipose areas where fat is not only useless but is also bad for health and looks unattractive. Muscular activity burns a part of accumulated fat while application of heat to specific areas of adipose tissue facilitates lipolysis, stimulates the body to use it and therefore reduces the fat in those areas.

Application of heat is preferably made by generators of infrared rays mounted on special supporting structures. To concentrate and direct the rays onto the body, the generators comprise a system of one or more lenses and have hinged tabs all round the edge of the lampholder. These generators are associated to the gymnastic apparatus either directly or by various means of support.

Special means enable them to assume the best position for treating the desired areas of the body of persons who are doing gymnastics or some muscular activity.

Generators can be placed at different heights and set in different directions and distances from the person; intensity can also be regulated as desired.

The generators of heat are mounted either on vertical up-rights with feet, so that they can be moved when needed, and the apparatus be set at different angles in relation to a horizontal axis, or on stands with a cross bar to carry the generators also set at different angles, but in this case in relation to a vertical axis.

Treatment can thus be given from the side or from above to a person engaged in muscular activity either free or on some gymnastic apparatus.

The heat generators, especially those producing infrared rays, comprise a universal fixing device with elastic pincers for application where needed on the structure of the gymnastic apparatus, in the best position for concentrating and directing the rays on the adipose tissues.

Alternatively these generators have a ring-type clamp to fit round tubular bars that form part of the structure of the gymnastic apparatus.

The generators of infrared rays may advantageously consist of a number of LEDs.

The LEDs are fixed onto flexible supporting material that can be worn by the human body undergoing fat-reducing treatment applied by means such as velcro strips, buckles, suction discs or others.

Said flexible support may be a band, a belt or the like, at whose ends are closing means such as pieces of velcro or some other material, and may be worn round the waist, round the thigh, on the abdomen or elsewhere.

The LEDs may be fed from a battery mounted on the supporting material which carries the LEDs themselves.

Preferably the LEDs are placed in contact with the body so that the rays are emitted straight onto the tissue. The gymnastic apparatus may be the bedroom 'bicycle', 'rowing machine' or a step machine, otherwise one for passive gymnastics.

The best effects that the invented process produces are obtained by an apparatus that comprises an oblong base and supports at one end a pedal machine with an electromagnetic brake and, at the other end an ergonomic armchair standing on a base. Above the armchair is a horizontal bar with guides along which a carriage moves and, by means of a toroidal ring, this carriage supports a set of infrared ray generators placed radially so that they practically surround the armchair.

Lying in the armchair the person starts the leg muscles working by pedalling on the pedal machine and at the same time receives infrared rays directed onto certain parts of the body.

The toroidal ring that carries the radial generators is connected to the carriage by an articulation with a transversal horizontal axis so that, by moving the carriage on its guides and causing the ring to turn on said articulation, the radial generators can be directed onto those parts of the body to be treated.

By turning on one, two or all the generators, the rays can further be regulated for treatment of said parts of the body.

The armchair can be adjusted axially by moving it along its rails in the base and also its inclination in relation to the person's body by causing it to rotate round a forward articulation on its base, to which it is connected, so that the person is placed in the best position in relation to the pedal machine.

Higher up, and opposite the position where the person's head lies, is an electronic unit comprising a monitor, a keyboard and an electronic card reader.

This unit is associated to another for diagnosis and for prescribing treatment comprising a computer with monitor, an electronic card writer with memory and various accessories such as a device for measuring folds, a gauge, tapemeasure and others.

Then, having evaluated subcutaneous fat by detection of cutaneous folds, having measured bone diameters and limb circumferences, this unit by means of a specific program makes a computerized analysis of the person's bodily composition and, with the aid of mathematical formulae devised for the purpose, works out a suitable plan of treatment. This plan indicates the areas of the body where fat should be reduced, the consumption of calories per minute in relation to the person's muscular consistency and the intensity of the physical exercise corresponding to the working heart rate which the person should maintain in order to use up the fat as a source of energy.

All necessary data for reducing fat, such as the working heart rate, duration of treatment in minutes, number of treatments, and anything else are written on the electronic card.

The patient starts the treatment by inserting the electronic card in the reader and, if necessary, typing on the keyboard any further instructions, corrections or additions to the plan of treatment.

The monitor informs and guides the person with images or written remarks.

The evident offers many evident advantages. By combining muscular activity with heat rays directed onto the adipose areas, these are reduced both by transformation of fat into energy and also by stimulating the body to reduce the fat in those areas.

As a result fat is reduced more quickly and effectively and, above all, this is done in certain areas. By making use of LEDs, applicable by contact with the human body as generators of infrared rays, said rays produce a direct effect inside the adipose tissues consuming a negligible quantity of energy, allowing the person to carry on physical activity either spontaneous or using gymnastic apparatus, said LED generators being applicable to the body by suitable means such as belts and others avoiding problems of bulk and offering maximum versatility of application.

All this can be done concentrating the maximum effects on just those parts of the body where it is most necessary to reduce adipose tissue, obtaining a high degree of interaction between muscular stimulus and that produced by direct thermal effect.

Characteristics and purposes of the invention will be made still clearer by the following examples of its execution illustrated by diagrammatically drawn figures.

FIG. 1 Perspective view of a stand type apparatus carrying a generator of infrared rays directed onto a person doing exercises on a flat surface.

FIG. 2 Detail of the infrared ray generator from one side.

FIG. 3 Detail of a system for intensifying infrared rays by means of lenses, longitudinal section.

FIG. 4 Detail of a system for directing infrared rays by means of orientable tabs, cut away longitudinally.

FIG. 5 The stand apparatus in FIG. 1 used by a person doing exercises lying on a mat, perspective view.

FIG. 6 The stand in FIG. 1 used by a person doing exercises aided by a stool, perspective view.

FIG. 7 A bedroom 'bicycle' with a thermofan mounted on the front upright, perspective view.

FIG. 8 Detailed perspective view of the thermofan.

FIG. 9 Rowing machine with two column-mounted infrared ray generators, one at each side, perspective view.

FIG. 10 Apparatus for exercising leg and arm muscles.

FIG. 11 Bedroom lever-type 'bicycle' used by a person standing up, associated to an infrared ray generator mounted on top of a rear upright, perspective view.

FIG. 12 Bedroom 'bicycle' with two generators of infrared rays one clipped onto the front upright and one on a rear support fixed to the base, perspective view.

FIG. 13 Detail of the infrared ray generator with mounting clip, perspective view.

FIG. 14 Detail of the generator connected to the clip by a flexible tube, perspective view.

FIG. 15 Front view of the diagnosis and prescription unit.

FIG. 16 Treatment unit, side view.

Figure 17:
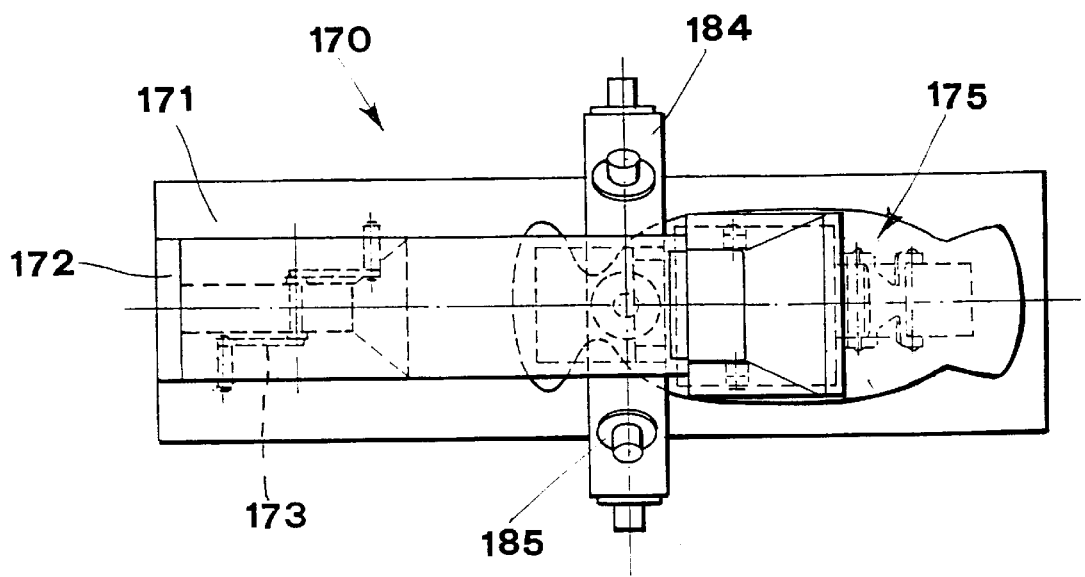

FIG. 17 Plan view of the unit in FIG. 16.

FIG. 18 As above, front view.

FIG. 19 Section of FIG. 18.

Figure 20:
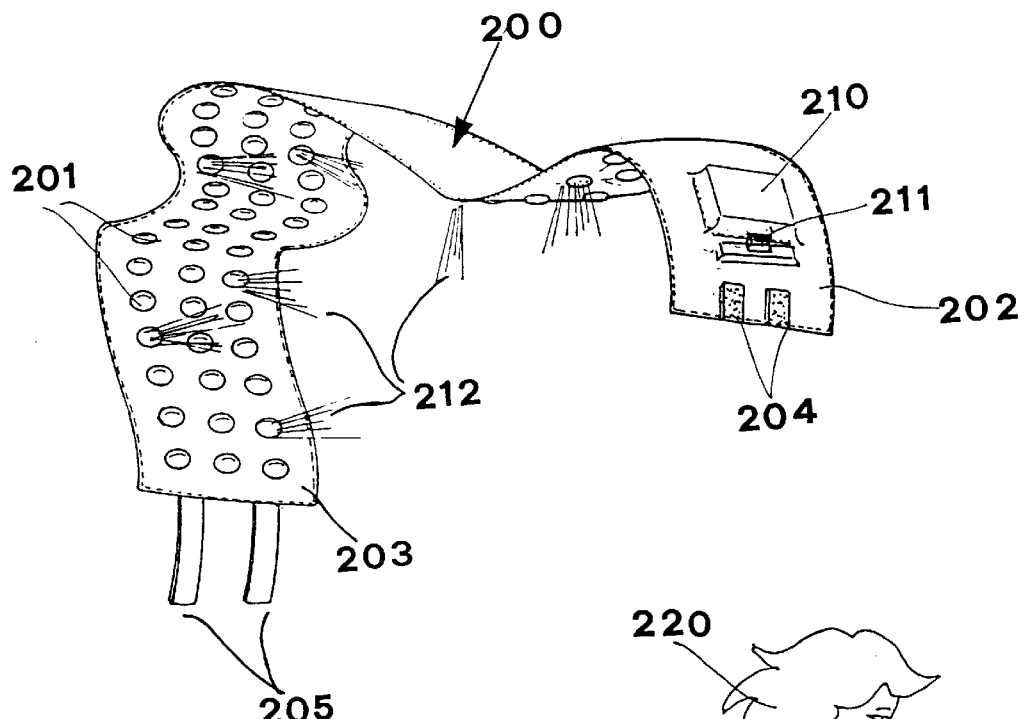

FIG. 20 A band of fabric, applicable to the body, with a number of LEDs on the inside, perspective view.

Figure 21:
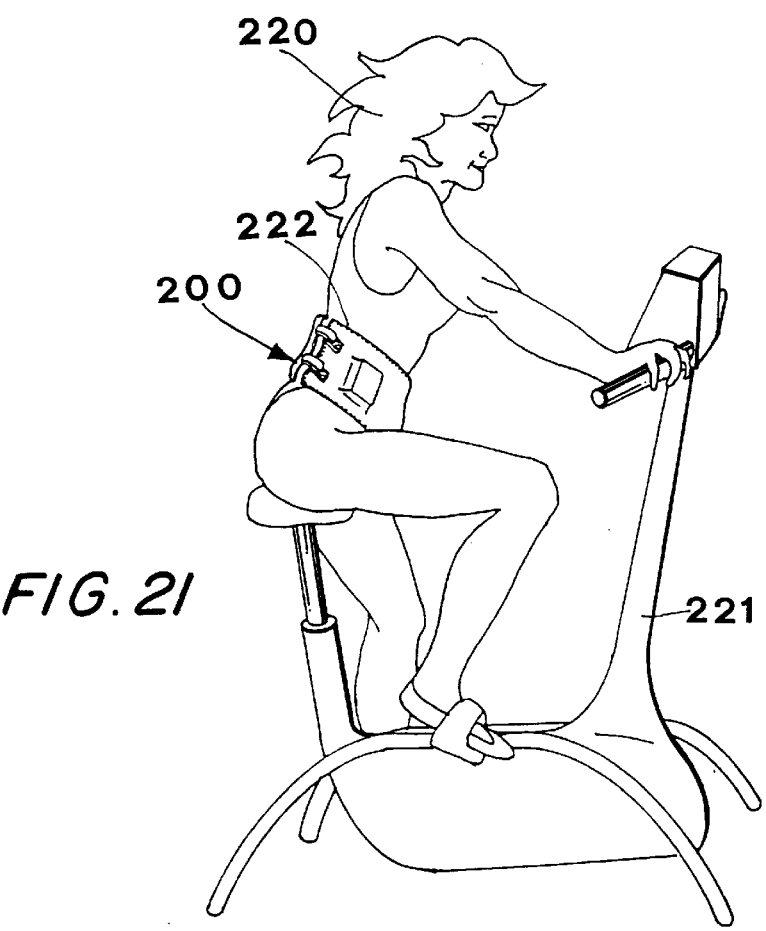

FIG. 21 The above band placed round the waist of a person doing exercises on a bedroom 'bicycle', perspective view.

FIG. 1 shows a table 10 on which a person 15 is doing exercises with the weight resting on knees and forearms. Across the table is placed a stand 20 with central cross bar 21 and inclined uprights 22 and 23 standing firmly on feet 24 and 25.

At the centre of the cross bar a plate 31 is mounted and to this is fixed the infrared ray generator 30 comprising an articulation 32 and lampholder 33 for the infrared ray lamp 34.

Main electricity is supplied through the cable 35 that comprises a ray intensity regulator 36 with potentiometer 37 and plug 38.

As clearly shown the infrared rays 39 heat the fat present under the surface of the buttocks of the person 15 while the muscular exercise raises the rate of heart beat to the best level for obtaining the desired results. The fat brought into play during muscular activity is mainly that in the area of the buttocks reached by the infrared rays that penetrate in depth.

Effective active action is thus created for reducing this fat by interacting movement and heat. Correct orientation of the lamp and regulation of ray intensity produces the maximum effect in a short time. FIG. 3 illustrates a generator of infrared rays 40 with a lampholder 41, connection 42 and comprising a set of lenses 43, 44 for concentrating rays from the lamp 48. Regulating means 45 and 46 for axial position of the lenses and focusing regulator 47 can be seen.

FIG. 4 illustrates a generator 50 of infrared rays with connection 51, comprising tabs 54 hinged to the forward edge 53 of the lampholder 52 for directing and concentrating the rays.

FIGS. 5 and 6 show people 60 and 70, one doing exercises on a mat 61 and the other on a gymnastic apparatus 71. The lamps 30, attached to the stands 20 send infrared rays 62 and 72 onto the abdominal areas 63 and 73 of the persons 60 and 70 respectively.

The subcutaneous fat on the abdomen is thus rapidly reduced by interaction between heat from the rays and muscular activity following the exercises.

In FIGS. 7 and 8 there is a bedroom 'bicycle' 80 with pedals 81 and front upright bar 82. On this bar is fixed the tubular thermofan 83 by a clip ring 85. This clip comprises the rounded fork 76 with threaded ends 87 onto which screw the wing nuts 88 to fix the clip onto the bar 82, and the articulation 89 to which is fixed the body of the thermofan 83. At its back is a motor-driven fan 90 and at the front are electric heating elements 91. Mains current is supplied through the cable 92 and the plug 93.

By means of the articulation 89, heat rays 95 can be directed towards the body of the person 94 engaged in muscular activity by working the pedals 81. Though hindered by low heat conductivity, interaction of the heat with the effects of muscular action greatly assists in reducing the fat in the areas reached by the heat rays.

FIG. 9 shows a bedroom rowing machine 100 with seat 101 and horizontal bar 102 at the top of the lever 103. The two generators 104, 105 work as a pair one on each side of the rower, and consist of uprights 106 with their bases 107 and 108 that support, by means of the articulation 109 the infrared ray lamps 111 and 112. Their height can be regulated using the holes 110 in the uprights 106. The rays strike the pelvic area of the person 113 whose arms are engaged in muscular activity.

In FIG. 10 a person 120 is sitting on the seat 121 of the gymnastic apparatus 119. This person's arms and legs are engaged in muscular activity both on the lower bar 122 and on the upper rings 124 fixed at the top of the shoulder support 123 which reacts elastically. In front of the person is the generator 125 supported through the articulation 126 by the upright 127 with its base 128.

The rays 129 strike the person in the areas chosen. FIG. 11 illustrates a lever-type 'bicycle' 130 with pedals 131, at the back of which is the upright 132 and at its top, through the articulation 134, the generator 133 with lamp 135 whose rays 136 are directed on the buttocks of the person 137 engaged in muscular activity.

FIG. 12 shows a bedroom 'bicycle' 140 onto which are mounted two infrared ray generators 142 and 152. The first is mounted on the front upright 141, held there by the pincers 144,with a spring 145, carrying the base of the lampholder 147 connected to the main electricity supply by the wire 148 and plug 149, said generator directing the rays 150 from the lamp 143 onto the body of the person 151 on the 'bicycle'.

Alternatively the lamp 143 can be fixed to the base 146 of the pincers 144 by the flexible tube 153 and lamp-holder 158.

This arrangement makes it possible to place the ray lamp in any position in relation to the person 151. The other generator 152 is fixed to the triangular support 154 fixed to the back of the 'bicycle' 140 by means of the articulation 155.

The lamp 156 directs rays 157 onto the buttocks of the person 151.

FIGS. 15–19 illustrate a system for treating localised excess fat, this system including a unit 160 for diagnosis and for prescribing treatment, and an apparatus 170 for giving the treatment.

The unit 160 for diagnosis and prescription in turn comprises a computer 161 with monitor 162, a printer 163, an electronic card writer 164, a memory and various accessories such as a fold measure, a gauge, and tape measure. The apparatus 170 for the treatment comprises a base 171 at one end of which is a framework 172 with ergometercycle 173 and electromagnetic brake controlled by a microprocessor 174 and an ergonomic reclining chair 175.

The framework 172 carries a horizontal crossbar 180 in which are guides 181 along which slides a carriage 182 that by means of a transversal articulation 183 supports a toroidal ring 184 on which are radially placed a set of infrared ray generators 185 so arranged as substantially to surround the reclining chair 175.

The microprocessor is connected to a keyboard 186, to a display 187, to an electronic card reader 188 and to a sensor of heart rate to be fitted onto the auricular lobe of the person receiving the treatment.

Under the reclining chair 175 is a base 190, a fixed support 191 with an articulation 192, and an adjustable strut 193 with an articulation 194.

A computerized analysis is made of the bodily composition of the person 195 undergoing treatment, using a specific program able to evaluate the extent of overweight and the amount of localised excess adipose tissue.

Subcutaneous fat is measured using the device to detect folds of fat, a gauge also measures bone diameters, and a tape measure limb circumferences. By means of special mathematical formulae, the computer program determines the person's bodily composition and supplies quantitative indications about those parts of the body where a reduction of localised fat would be advisable.

A calculation is also made of the intensity of physical exercise corresponding to the working heart rate that the person must maintain in order to use up the fat as a source of energy. The practical method generally used to establish the aerobic intensity of training consists of calculating 70% of the person's range of working heart beat:

Therefore from HRr=Heart Rate at rest and from max HR=maximum Heart Rate=220–age, we obtain the HRt= Heart Rate in training by the formula:

$$HRt=HRr+0.70(maxHR-HRr).$$

The program also indicates consumption of calories (based on the person's muscular consistency) per minute at the calculated heart rate.

If, for example, the person should lose 500 grams of fat and can, with physical activity of an intensity that produces 140 heart beats per minute, "burn up" 12 calories per minute, considering that body fat supplies about 7 calories for every gram, that person will burn, in 40 minutes of activity, 480 calories equivalent to about 68 grams of fat.

Therefore, if the person used only fat as a source of energy, only 7.3 treatments of 40 minutes each would be necessary (500÷68=7.3).

But considering that in the first few minutes of training other sources of energy, such as sugar, are used, this means that 10 treatments may be necessary.

When the computerized analysis of bodily composition, in which it is laid down the quantity of fat to eliminate and the area, or areas,of the body from which it should be removed, the person is informed of the number of treatments required, their duration and intensity of training.

All this information is printed out by the printer connected to the computer.

A writing device writes down on an electronic card all the data needed for elimination of fat (working heart rate, time in minutes of each treatment and their number). To begin treatment in the specific piece of apparatus 170, the person 195 adjusts the position of the chair 175 according to height and position and to inclination of the toroidal ring 184 carrying the infrared ray generators 185, inserts his electronic card in the reader 188, lies down, attaches the heart beat sensor to his ear and starts to pedal on the machine watching the monitor 187 of the computer 188 that keeps him informed.

The microprocessor 174 reads, from the ear-mounted sensor, the heart rate of the person 195 while pedalling and automatically adjusts braking (if the heart rate is lower, braking force increases, if the heart rate is higher, braking force diminishes) in order to maintain the heart rate constant. The person then completes the period of training always guided by the monitor 187.

FIG. 20 shows a band 200 of fabric onto the inside of which are fixed a quantity 201 of LEDs giving off infrared rays, there being at the ends 202, 203, strips of velcro 204, 205 with which the band can be comfortably fitted onto the person's body.

The LEDs are connected to an independent supply of electricity 210 operated by the switch 211.

The LEDs emit infrared rays 212 that can penetrate directly into the body as the band is used with the LEDs inside. In FIG. 21 the person 220 is working on the bedroom 'bicycle' 221 and is wearing the LED band 200 round her waist 222 so that the infrared rays stimulate the adipose tissue stimulated at the same time by the physical exercise.

By means of continuous physical exercise (pedalling) and with a heart rate kept constant, together with the effect of infrared rays, the use of fat in the areas of the body subjected to rays is stimulated reducing the amount of fat in excess in those areas.

I claim:

1. A process for reducing localized adipose tissue in a human body, comprising the steps of stimulating lipolysis in areas of adipose tissues by heat from generators of infrared rays; providing gymnastic equipment with which a user carries out muscular activity of an aerobic kind; and arranging the generators so that they provide a best position, concentration and orientation of heat on the adipose tissues of the user, said arranging includes connecting the heat generators by a clip and a ring to go around tubular parts of the gymnastic equipment.

2. A process for reducing localized adipose tissue in a human body, comprising the steps of stimulating lipolysis in areas of adipose tissues by heat from generators of infrared rays; providing gymnastic equipment with which a user carries out muscular activity on an aerobic kind; arranging the generators so that they provide a best position, concentration and orientation of heat on the adipose tissues of the user, said providing including providing the gymnastic equipment which includes a base which carries at one end a pedal device with an electromagnetic brake and at the other end an ergonomic reclining chair, with a horizontal bar arranged at a higher level than the chair and provided with guides for sliding on an undercarriage and with a ring, said arranging including arranging a set of the generators radially on the ring so that the generators substantially surround the reclining chair, while the user lying on the chair stimulates muscles of buttocks by pedaling on the pedal device with simultaneous directing the infrared rays on chosen parts of a user's body; moving and orienting the ring and the chair; and turning on selectively some or all of the generators.

3. A process as defined in claim 2; and further comprising providing a unit for diagnosis and prescription comprising a computer with a monitor, an electronic card writer with a memory, and accessories including a fold measuring device, a gauge and a tape measure; measuring by said unit some subcutaneous fat by detection of cutaneous folds, measurement of bone diameters and limb circumferences; providing a computerized analysis of a bodily composition of the user; and preparing programs for indications with regard to areas of a body of the user where fat should be reduced, with regard to consumption of calories per minute in relation to a muscular consistency of the user, and with regard to an intensity of physical exercise corresponding to a heart rate during work which the user should maintain in order to use his fat as a source of energy; and writing all necessary data on an electronic card by the electronic card writer.

4. A process for reducing localized adipose tissue in a human body, comprising the steps of stimulating lipolysis in areas of adipose tissues by heat from generators of infrared rays; providing gymnastic equipment with which a user carries out muscular activity on an aerobic kind; arranging the generators so that they provide a best position, concentration and orientation of heat on the adipose tissues of the user; and arranging an electronic unit above and opposite a position where a head of the user rests and providing in the electronic unit a display, a keyboard and an electronic card reader so that the user can start a treatment by inserting a personal electronic card into the reader; providing on the card a memory for memorizing data needed for reducing fat of the user and selected from the group consisting of a working heart rate, a duration in minutes, and a number of treatments; introducing instructions, corrections or additions into a keyboard of the electronic unit; and displaying on the display images and words for information and guidance of the user throughout the treatment.

5. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues, said equipment including vertical uprights with bases on which the generators are placeable in desired positions at different heights and at different angles in relation to a horizontal axis.

6. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues, said equipment including stands with cross bars, said heat generators being settable along said cross bars at different angles in relation to a vertical axis.

7. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues, said equipment having tubular parts, said generators having an attachment with a clamp and a ring for fixing said generators to said tubular parts of said equipment.

8. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues, said equipment having a main oblong base having two ends, a pedaling device supported on one of said ends and provided with an electromagnetic brake, a reclining chair arranged on the other of said ends, a horizontal bar arranged above said chair and provided with guides, an undercarriage sliding in said guides and having a ring, said generators being set radially in said ring so that said generators surround said chair and so that the user lying on said chair can exercise buttock muscles by using said pedal device.

9. An apparatus as defined in claim 8, wherein said ring is connected to said carriage by an articulation with a transverse horizontal axis so that by moving said carriage along said guides and causing said ring to turn on said articulation, the generators are directed onto parts of a body of the user to be treated, at least some of said generators being turnable to regulate the rays received by the parts of the user's body.

10. An apparatus as defined in claim 8, wherein said base is provided with rails, said chair being formed as reclining chair and having a base portion slideable on said rails so as to axially adjust said chair, said base portion being connected to a forward articulation around which said chair can turn so as to adjust inclination of a body of the user so that the user can assume a best position for working said pedal device.

11. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues; an electronic unit arrangeable above and opposite a position at which a head of the user rests and having a display, a keyboard and an electronic card reader; a personal electronic card insertable into said electronic card reader for starting a treatment and provided with data needed for the treatment selected from the group consisting of a working heart rate, a duration in minutes and a number of treatments, so that instructions, corrections and additions to the treatment can be typed on said keyboard, and the user is informed and guided during a course of the treatment by images and writing on said display.

12. An apparatus for reducing localized adipose tissue in a human body, comprising generators of infrared rays for stimulating lipolysis of areas of adipose tissues by heat; gymnastic equipment with which a user carries out muscular activity of an aerobic kind; and means for arranging said generators on said gymnastic equipment so that said generators provide a best position, concentration and orientation of heat on the adipose tissues; and a unit for diagnosis and for prescribing treatment and including a computer with a monitor, an electric card writer with a memory store and accessories including a fold measuring device, a gauge, and a tape measure, said unit after measuring subcutaneous fat by detecting subcutaneous folds, bone diameters, and limb circumferences, provides a computerized analysis of a bodily composition of the user and then prepares a program indicating which parts of a body of the user should be given fat-reducing treatment, what caloric consumption per minute in relation to a muscular consistency of the user and an intensity of physical exercise corresponding to a working heart rate which the user should maintain in order to use up fat as a source of energy, all data needed for reduction of fat selected from the group consisting of a working heart rate, a duration of treatment in minutes, and a number of treatments being written on said electronic card by a writing device.

\* \* \* \* \*